United States Patent [19]

Broyles et al.

[11] Patent Number: 5,735,437
[45] Date of Patent: Apr. 7, 1998

[54] LOCKABLE, HAND-HELD DISPENSER AND MIXING TRAY FOR DISPENSING SMALL QUANTITIES OF MATERIAL

[75] Inventors: Bruce R. Broyles, Oakdale; James A. Wilson, North St. Paul; Vern E. Radewald, Birchwood; James C. Biesecker, Eagan, all of Minn.

[73] Assignee: Minnesota Mining and Manufacturing, St. Paul, Minn.

[21] Appl. No.: 655,051

[22] Filed: May 29, 1996

Related U.S. Application Data

[63] Continuation of Ser. No. 589,818, Jan. 22, 1996, abandoned.

[51] Int. Cl.⁶ .................................................. B67D 5/52
[52] U.S. Cl. ................ 222/137; 222/153.13; 222/391; 222/420; 433/89
[58] Field of Search ................. 222/137, 153.13, 222/420, 421, 391, 485; 433/77, 79, 89, 90; 206/1.7

[56] References Cited

U.S. PATENT DOCUMENTS

| | | | |
|---|---|---|---|
| D. 291,178 | 8/1987 | Toms | D9/424 |
| D. 361,594 | 8/1995 | Salis | D9/341 |
| D. 369,469 | 5/1996 | Gregory | D9/424 |
| 3,132,772 | 5/1964 | Bristow | 222/181 |
| 3,221,409 | 12/1965 | Thiel et al. | 32/60 |
| 3,517,668 | 6/1970 | Brickson | 128/218 |
| 3,977,574 | 8/1976 | Thomas | 222/391 |
| 4,444,560 | 4/1984 | Jacklich | 222/391 |
| 4,457,712 | 7/1984 | Dragan | 222/391 |
| 4,472,141 | 9/1984 | Dragan | 433/90 |
| 4,569,662 | 2/1986 | Dragan | 433/89 |
| 4,708,650 | 11/1987 | Holewinski et al. | 433/90 |
| 4,710,178 | 12/1987 | Leonard et al. | 604/209 |
| 4,779,770 | 10/1988 | Herold | 222/391 |
| 4,820,287 | 4/1989 | Leonard | 604/209 |
| 4,991,749 | 2/1991 | Kay et al. | 222/384 |
| 5,295,827 | 3/1994 | Fundingsland et al. | 433/77 |
| 5,377,823 | 1/1995 | Steen et al. | 433/79 |

FOREIGN PATENT DOCUMENTS

| | | | |
|---|---|---|---|
| 0 109 913 | 5/1984 | European Pat. Off. | |
| 2212768 | 7/1974 | France | |
| 406100054 | 4/1994 | Japan | 222/137 |
| 669 577 | 3/1989 | Switzerland | |

Primary Examiner—Philippe Derakshani
Attorney, Agent, or Firm—James D. Christoff

[57] ABSTRACT

A dispenser for dispensing relatively low viscosity material includes a plunger that is movable to advance the plunger in the chamber. A full stroke of the lever dispenses no more than a single drop of material from the chamber. A cap is detachably connected to an outlet of the chamber and includes an arm in contact with the lever when the cap is connected to the outlet for releasably retaining the lever in a fixed position to prevent unintentional discharge of material from the chamber. A stop comprising one or more sets of teeth is connected to the lever for hindering advancement of the plunger after the lever is released. In certain embodiments, the dispenser includes two side-by-side chambers, and a mixing tray has a well with side recesses for receiving protruding outlets of the chambers.

24 Claims, 4 Drawing Sheets

LOCKABLE, HAND-HELD DISPENSER AND MIXING TRAY FOR DISPENSING SMALL QUANTITIES OF MATERIAL

This application is a continuation application of U.S. application Ser. No. 08/589,818, fled Jan. 22, 1996.

BACKGROUND OF THE INVENTION

1. Field of the Invention

This invention relates to a hand-held dispenser having an actuating lever that is movable to advance a plunger for dispensing material from one or more chambers. The invention also relates to a mixing tray especially adapted for use with a hand-held dispenser.

2. Description of the Related Art

A variety of hand-held dispensers are available for dispensing material to a selected location. Many dispensers include a dispenser body having inner walls that define one or more chambers for containing a quantity of the material to be dispensed. Other dispensers have a receptacle for detachably receiving a removable cartridge that has one or more material-containing chambers.

A large number of hand-held dispensers have a plunger that is advanced toward each chamber to eject and dispense the contained material when desired. In some dispensers, a lever is pivotally connected to the dispenser body. A ratchet mechanism connected to the lever is operable to advance the plunger and dispense material from the chamber or chambers when the lever is depressed.

Some lever-operated dispensers are adapted to dispense two materials simultaneously from two side-by-side chambers that are either contained within the dispenser body or contained within a cartridge that is detachably connected to the dispenser body. In such dispensers, the plunger includes a pair of interconnected plunger rods that simultaneously advance toward respective chambers as the lever is depressed. These dispensers are particularly useful for compositions made of two components or materials that are typically not mixed together until immediately prior to use.

Examples of compositions made of two or more materials that are usually not mixed together until use include adhesives (such as epoxies), coatings and sealants for use in industrial, commercial and household applications. Other examples include medical and dental compositions such as self-curing CONCISE brand white dental sealant (from 3M). Dispensers having two chambers are especially useful for materials that begin to cure when mixed together, or for materials that are unstable when mixed and might degrade if supplied as a single component.

Some dispensers are particularly adapted to dispense relatively small amounts of material having a relatively low viscosity. Examples of such dispensers are described in U.S. Pat. Nos. 3,977,574, 4,444,560 and 4,779,770. When such dispensers are used in the field of dentistry, however, a larger quantity of material than actually desired may be dispensed. For example, the dental practitioner may need less than a single drop of material, a quantity that is difficult to accurately obtain using conventional dispensers.

Dispensers having one or more relatively long chambers typically include a relatively long plunger that is movable over substantially the entire length of the chambers. However, the chambers are often filled by the manufacturer with the material to be dispensed before being shipped to the end user. As a consequence, the plunger of such dispensers often extends a considerable distance rearwardly of the dispenser body, at least until such time that the majority of the material in the chambers has been dispensed.

Unfortunately, the rearwardly extending plunger of such dispensers is prone to being bumped, jarred or otherwise moved before the intended dispensing operation, such that a quantity of material may be ejected from the outlet of the chambers. Such unintended dispensing may occur, for example, during shipment of the dispenser to the end user or during handling or storage of the dispenser in the user's facility, as may occur when the dispenser is stored loosely in a drawer and comes into contact with other items. As can be understood, material that is unintentionally dispensed typically constitutes waste and often creates a spill that is a nuisance to clean. Moreover, if the material in the chamber has a relatively low viscosity such as a viscosity similar to water, the plunger may be moved forward and cause the material to be ejected even if only a relatively light impact force is applied against the rear end portion of the plunger.

SUMMARY OF THE INVENTION

The present invention in one aspect relates to a dispenser adapted to precisely dispense only a single drop or less of material from each material-containing chamber. In one embodiment, the dispenser comprises a body and a first chamber connected to the body for containing a quantity of material to be dispensed. The first chamber includes an outlet and a liquid material is received in the chamber. A plunger is connected to the body and is movable relative to the body in an advancement direction toward the chamber, and the plunger includes a number of teeth arranged in a row. A lever is pivotally coupled to the body and is movable relative to the body between a released position and a fully depressed position. A pawl is provided for engagement with the teeth, and the lever is connected to the pawl for advancing the plunger as the lever is moved from the released position to the fully depressed position. The pawl moves over only a single tooth as the lever moves from a fully depressed position to the released position. Movement of the lever from the released position to the fully depressed position enables no more than a single drop of material to fall from the outlet.

The present invention also overcomes the problems noted above with respect to prior art dispensers by provision of a dispenser that has locking structure for precluding movement of a dispensing lever when desired. As a consequence, the dispenser can be safely shipped to the end user and then handled or stored by the end user with little, if any, likelihood that material will be unintentionally dispensed and wasted.

More particularly, the dispenser in accordance with another aspect of the invention comprises a body and a first chamber connected to the body for containing a quantity of material to be dispensed, wherein the first chamber includes an outlet. A plunger is coupled to the body and is movable relative to the body in an advancement direction toward the chamber. A lever is pivotally connected to the body and is movable relative to the body between a first position and a second position. The lever is connected to the plunger for advancing the plunger as the lever is moved from the first position to the second position. A cap is detachably connected to the outlet. The cap includes an arm in contact with the lever when the cap is connected to the outlet for releasably retaining the lever in the first position.

Another embodiment of the invention concerns a dispenser that comprises a body and a first chamber connected to the body for containing a quantity of material to be dispensed, wherein the first chamber includes an outlet. A plunger is coupled to the body and is movable relative to the body in an advancement direction toward the chamber. A lever is pivotally connected to the body and is movable relative to the body between a first position and a second position. The lever is coupled to the plunger for advancing the plunger as the lever is moved from the first position to the second position. A stop is connected to the lever for contact with the plunger in order to substantially preclude advancement of the plunger when the lever is in the first position.

The present invention also concerns an improved mixing tray especially adapted for use with a dual chamber dispenser. The mixing tray comprises a substrate having an upper, generally horizontal wall section, side wall sections depending from the upper wall section and a bottom wall section that is connected to the side wall sections. The side wall sections and the bottom wall section define a mixing well having a certain volume. The substrate also includes wall portions depending from the upper wall section and presenting a pair of recesses located along the side wall sections. Each of the recesses has a volume that is less than the volume of the mixing well, and each recess is in communication with the mixing well. Each recess is located above the bottom wall section to enable material to be dispensed into the recesses to flow by gravity into the well.

These and other features of the invention are described in more detail in the description of the presently preferred embodiments that follows.

DETAILED DESCRIPTION OF THE PREFERRED EMBODIMENT

Figure 1:
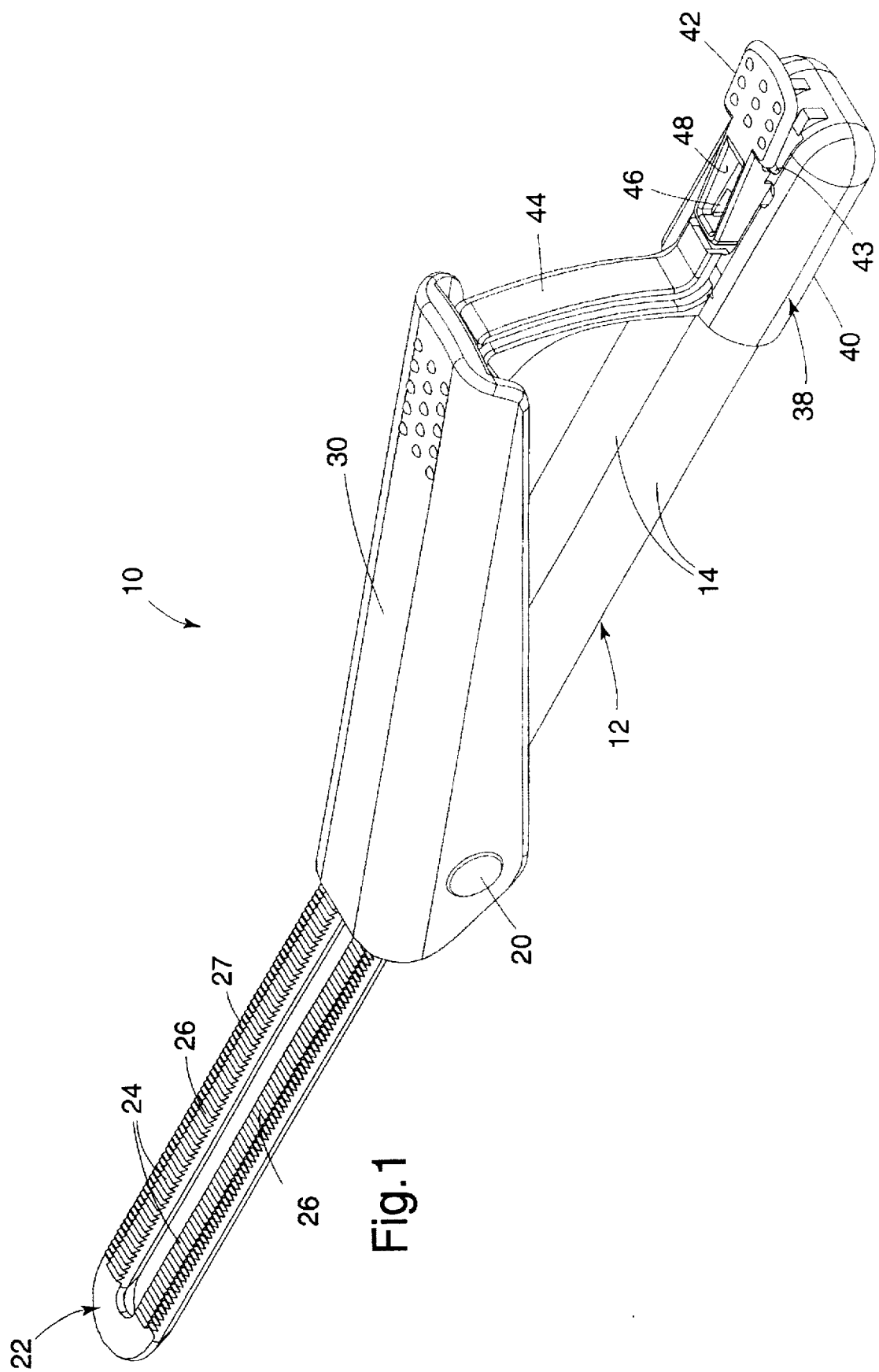
FIG. 1 is a top, left side and front isometric view of a dispenser that is constructed according to a presently preferred embodiment of one aspect of the invention.
Figure 2:
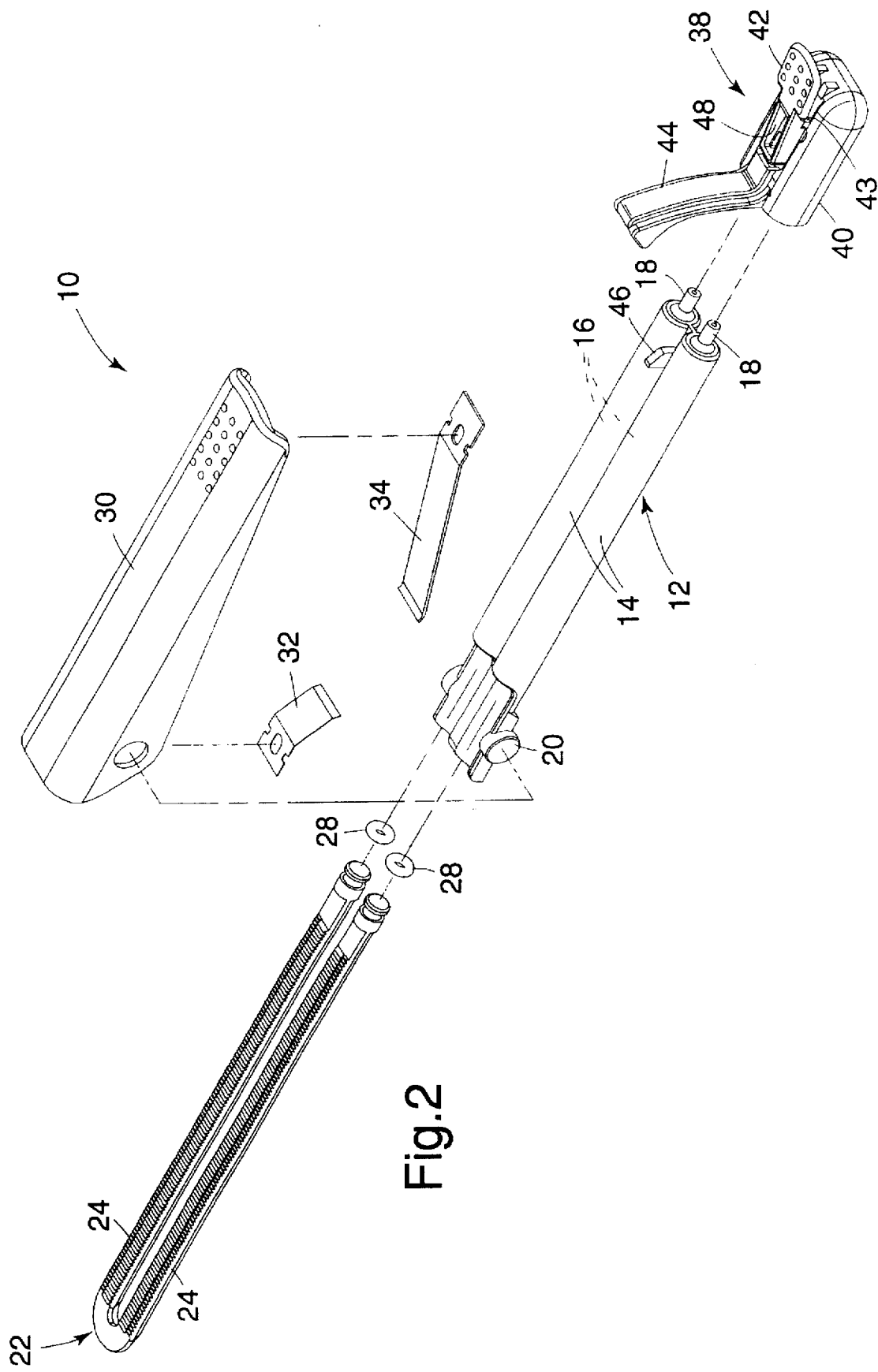
FIG. 2 is a view somewhat similar to FIG. 1 except that the dispenser is shown in exploded form.

A dispenser that is constructed in accordance with the principles of one embodiment of the present invention is shown in FIGS. 1–3 and 6 and is designated broadly by the numeral 10. The dispenser 10 includes a body 12 having a pair of elongated, side-by-side containers 14 that extend in directions parallel with respect to each other. Each container 14 has inner wall surfaces that define a generally cylindrical chamber 16 (FIG. 2). Preferably, the chamber 16 has a relatively small diameter and a relatively long overall length.

Each container 14 includes a protruding front outlet 18 having an outlet opening that is in communication with the respective chamber 16. The containers 14 are integrally connected to each other by a web that extends in a reference plane containing the central longitudinal axes of the containers 14. A rear end portion of the body 12 includes a pair of cylindrical pivot bosses 20 that each have a central axis. The central axes extend in a direction parallel to the same reference plane and also extend in a direction perpendicular to the longitudinal axes of the containers 14.

The dispenser 10 also includes a generally U-shaped plunger 22 having a pair of spaced apart plunger rods 24 that extend in directions parallel with respect to each other. As depicted in FIG. 2, each plunger rod 24 includes a generally cylindrical front end portion having a circumscribing groove that receives an O-ring 28. Each plunger rod 24 has an upper surface with a first, inner row of teeth 26 and a second outer row of teeth 27 that lies in side-by-side relation to the inner row of teeth 26.

Figure 3:
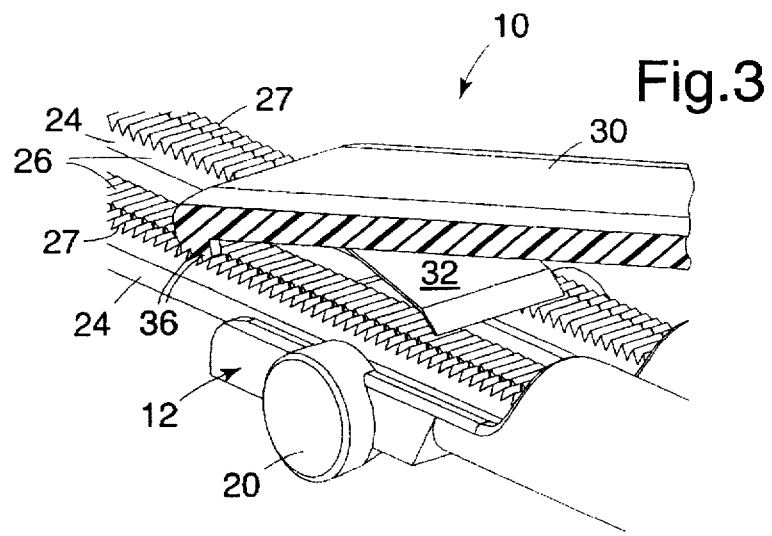
FIG. 3 is an enlarged top, left side and front isometric view of a portion of the dispenser illustrated in FIG. 1, with parts cut away in section.

The rows of teeth 26, 27 are illustrated in more detail in FIG. 3. Preferably, the teeth of the inner rows of teeth 26 are inclined rearwardly (i.e., when the plunger 22 is held in a position extending in a horizontal plane, the rear wall of each tooth is nearer to a vertical orientation than the front wall of the same tooth). On the other hand, the teeth of the outer rows of teeth 27 are preferably inclined forwardly (i.e., the front wall of each tooth is nearer to a vertical orientation than the rear wall of the same tooth when the plunger 22 is held in a horizontal position).

Figure 6:
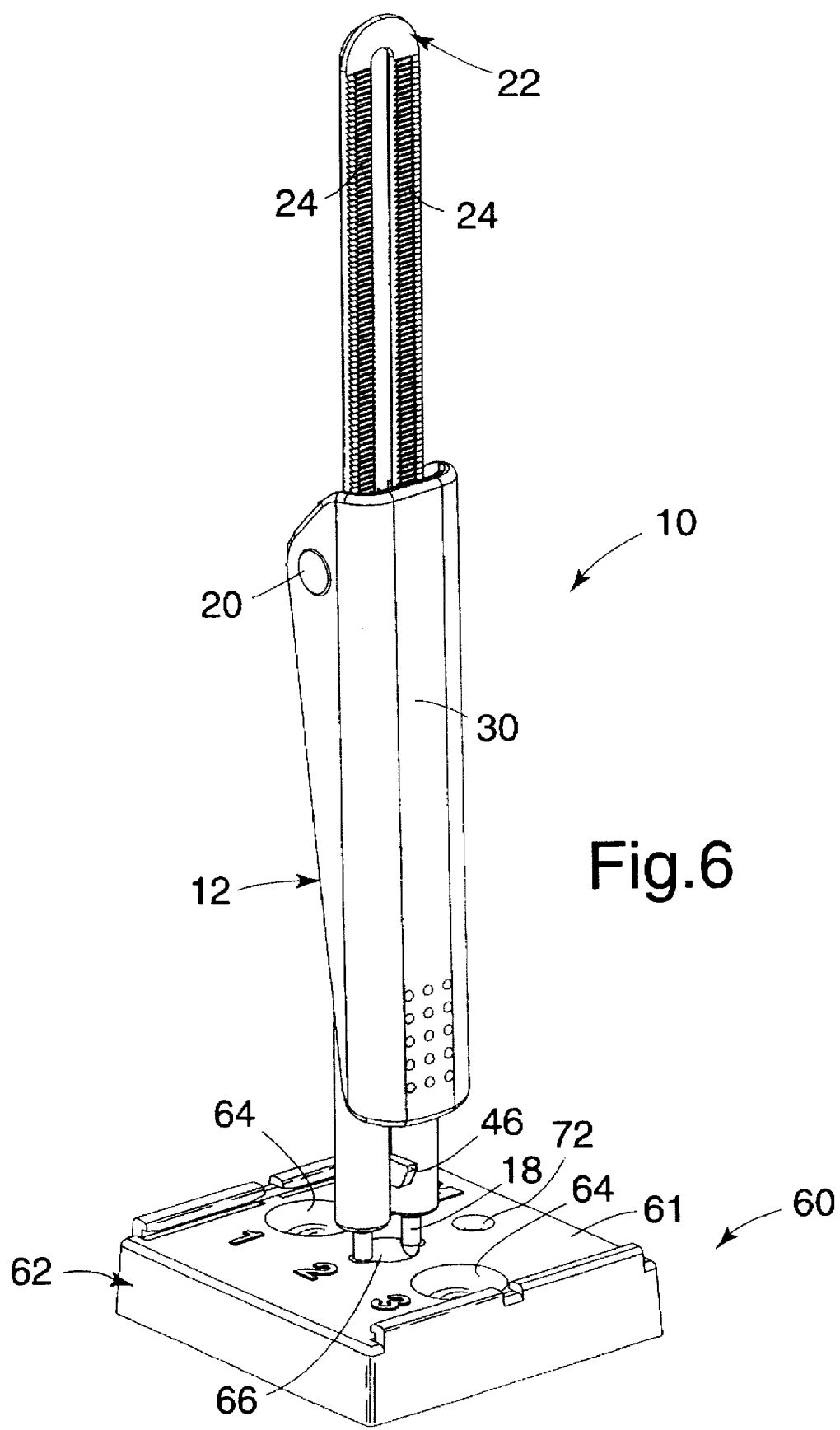
FIG. 6 is a view of the mixing tray shown in FIGS. 4 and 5 along with the dispenser shown in FIGS. 1–3, illustrating use of the dispenser and the tray during a dispensing operation, and wherein a cap of the dispenser has been removed and a lever of the dispenser has been moved to a second position.

A lever 30 has a pair of spaced apart depending side walls that each include a circular opening (see, e.g., FIG. 2). When the lever 30 is assembled to the body 12, each pivot boss 20 extends through a respective one of the openings in order to pivotally connect the lever 30 to the body 12. The side walls of the lever 30 are flexibly deformed in an outwardly direction during assembly to pass over each pivot boss 20. The lever 30 is movable between a first, released position (such as is shown in FIG. 1) and a second, fully depressed position (such as is shown in FIG. 6).

A spring steel pawl 32 (FIGS. 2 and 3) is connected to an underside surface of the lever 30. When the lever 30 is depressed by the operator and moved from the first position to the second position, the front, lower end of the pawl 32 engages a tooth of each of the inner rows of teeth 26 and urges the plunger 22 in a forward, advancement direction toward the front end of the chambers 16. As the plunger 22 is so moved, the plunger rods 24 together with the O-rings 28 eject material in the chambers 16 through respective outlets 18.

A steel spring 34 (FIG. 2) is also connected to an underside surface of the lever 30 and has a lower end portion that slidably engages a top surface of the containers 14. When the operator releases the lever 30, the spring 34 moves the lever 30 from the second position back to the first position. As the lever 30 returns to the first position, the front end of the pawl 32 rides over the two teeth of the rows of teeth 26 previously contacted for advancement of the plunger 22 and then comes into contact with the next adjacent tooth of each plunger rod 24 located rearwardly of the two previously contact teeth. Each full stroke depression of the lever 30 (i.e., from the first position to the second position) advances the plunger 22 only a distance equal to the spacing between adjacent teeth in the rows of teeth 26.

As shown in FIG. 2, the top, rear wall of each container 14 stops short of the rear end of the body 12 to enable the lower end of the pawl 32 to contact the rows of teeth 26.

Preferably, the O-rings 28 provide sufficient frictional resistance to movement of the plunger 22 so that the lower end of the pawl 32 can ride over the teeth when the lever 30 is released and enable the pawl 32 to contact the next adjacent teeth located in a rearwardly direction.

However, when the lever 30 is released, the forwardly-directed force previously exerted on the plunger 22 is also released and the plunger 22 moves a slight distance in a rearwardly direction. Such slight rearward movement is probably due in part to the resiliency of the O-rings 28 and also to the rearward, sliding motion of the pawl 32 over the rows of teeth 26. Rearward movement of the plunger 22 provides a small negative pressure in the chambers 16 that slightly draws back material in the outlets 18 in a direction toward the respective chambers 16. The drawback of material from the outlets 18 advantageously reduces the amount of material present at the outlet openings and consequently reduces the likelihood that the material will inadvertently ooze from the outlet openings.

The dispenser 10 is adapted to dispense no greater than a single drop of material per full stroke of the lever 30 and preferably less than a single drop of material per full stroke of the lever 30. For example, when the chamber 16 has an inner diameter of 0.203 inch (5.15 mm), and the distance between the teeth in the rows of teeth 26 is 0.031 inch (0.78 mm) (which is also equal to the distance the plunger 22 advances when the lever 30 is moved from the first position to the second position), only 0.001 cu. in. (0.016 ml) of material is dispensed from each chamber 16. Preferably, the amount of material dispensed from each chamber 16 per full stroke is no greater than a single, free-falling drop, and more preferably is less than a single, free-falling drop.

Preferably, the pawl 32 and the spring 34 are attached to the lever 30 by respective, small posts that depend from the underside of the lever 30. Each post passes through an opening (see FIG. 2) in the upper portion of one of the pawl 32 and the spring 34, and is then staked by heat and pressure to form an enlarged, rivet-like head. Thereafter, the heads retain the pawl 32 and the spring 34 in secure connection to the lever 30.

A rear end of the lever 30 is integrally connected to a pair of stops, each of which comprises a set of three teeth 36 (FIG. 3). The teeth 36 extend in a direction parallel to the teeth of the rows of teeth 26, 27. One set of teeth 36 is located above one row of teeth 27 and the other set of teeth 36 is located above the other row of teeth 27. When the lever 30 is in the first position, the teeth 36 meshingly engage grooves between adjacent teeth of each row of teeth 27 and substantially preclude movement of the plunger 22 in a forward direction.

As a result, the teeth 36 substantially prevent advancement of the plunger 22 once the lever 30 is released and once the spring 34 has returned the lever 30 to the first position. Consequently, if the rear end portion of the plunger 22 is accidentally bumped or is otherwise urged in a forward direction, the teeth 36 retain the plunger 22 in a fixed position relative to the body 12 so that material is not dispensed from the chambers 16.

The dispenser 10 also includes a cap 38 that is illustrated in FIGS. 1–2. The cap 38 includes a housing 40 and forwardly extending, upper handle 42 that is pivotally and integrally connected to the housing by a pair of small, flexible bars 43 that extend away from each other. One of the bars 43 is depicted in FIGS. 1 and 2. The handle 42 includes a forward, finger engageable surface having a series of bumps to facilitate the user's grip on the cap 38.

The cap 38 also includes a lever locking structure that comprises an arm 44 connected to the housing 40. The arm 44 extends in an upwardly and a rearwardly direction. When the cap 38 is connected to the body 12, an upper end section of the arm 44 contacts the underside of the front portion of the lever 30 as shown in FIG. 1. When the cap 38 is connected to the body 12 in such a manner, the arm 44 releasably locks and retains the lever 30 in its first position and essentially precludes the lever 30 from moving from the first position to the second position. Moreover, when the cap 38 is so connected, the arm 44 helps prevent advancement of the plunger 22 since the arm 44 retains the lever 30 in the first position where the teeth 36 are in firm, meshed engagement with teeth of the two rows of teeth 27.

An upright tab 46 is integrally connected to the web that extends between the two containers 14. When the cap 38 is coupled to the body 12 in the manner shown in FIG. 1, the tab 46 is received in a hole 48 located in a rear portion of the handle 42. The tab 46 and the hole 48 provide a means for releasably locking the cap 38 in a position coupled to the body 12.

To remove the cap 38 from the body 12, the forward surface of the handle 42 is depressed such that the handle 42 pivots about the webs 43 until the hole 48 has been raised to a position sufficient to clear the tab 46. Advantageously, the protruding tab 46 also helps insure that the cap 38 is connected to the body 12 in the orientation shown in FIG. 1 and not in an opposite orientation wherein the arm 44 extends away from the lever 30.

The cap 38 also includes a pair of foam pads (not shown) disposed within the housing 40 and retained in place by friction. The pads are spaced apart from each other by means of a relatively short dividing wall located within the housing 40. The pads contact the front ends of the outlets 18 when the cap 38 is received on the body 12 in order to seal the outlet openings.

The keying structure presented by the tab 46 also insures that the outlet 18 of one container 14 always contacts the same pad whenever the cap 38 is connected to the body 12. If, for example, a small amount of material from one of the chambers 16 is present on the corresponding pad when the cap 38 is removed from the body 12, such material will not come into contact with the outlet 18 of the other chamber 16 whenever the cap 38 is reattached to the body 12. As a result, the likelihood of cross-contamination of material from the two chambers 16 is substantially reduced.

Preferably, one of the plunger rod 24 is marked with a series of indicia that can be visually compared to a suitable reference location on the body 12, such as an arrow next to a small slotted opening of the body rearwardly of the pivot bosses 20 and adjacent the marked plunger rod 24. The indicia provide an indication of the extent that the plunger 22 has advanced so that the user is informed of the quantity of material that remains in the chambers 16. If desired, the indicia may comprise a series of numerals that represent the number of remaining "clicks" or depressions of the lever 30 that can occur before the plunger 22 has reached its limit of travel in a forward, advancement direction.

Preferably, the body 12, the lever 30 and stop 36, the plunger 22 and the cap 38 are made of strong, stiff synthetic resinous materials. Suitable materials for the body 12 include high density polyethylenes, such as MARLEX brand polyethylene resin, no. HMN55180, from Phillips Chemical Company. Suitable materials for the plunger 22, the lever 30 and the cap 38 include polypropylene filled with glass fibers, such as MAXXAM brand polypropylene resin, no. SB-418-

G001, from M. A. Hanna. The O-rings 28 and the foam pads are preferably made of ethylene propylene diene monomer (EPDM), and the pawl 32 and the spring 34 are preferably made of type SAE 30301 stainless steel.

Figure 4:
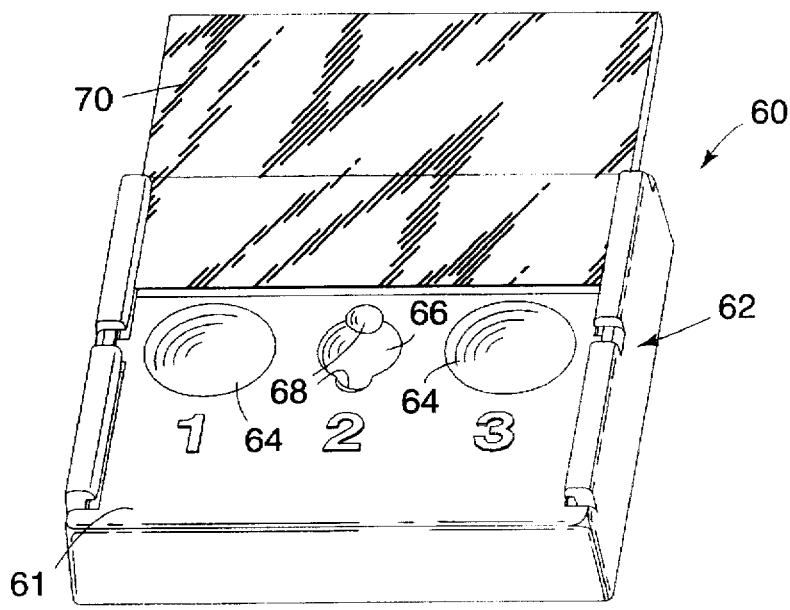
FIG. 4 is a top, right side and front isometric view of a mixing tray according to another aspect of the invention that is preferred for use with the embodiment of the dispenser depicted in FIGS. 1–3.
Figure 5:
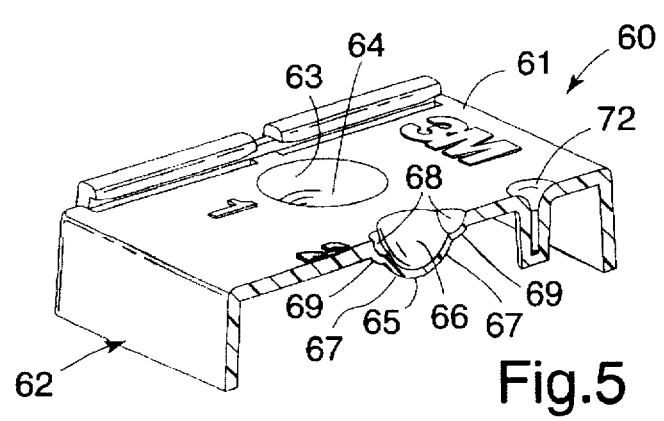
FIG. 5 is a view somewhat similar to FIG. 4 except that FIG. 5 is taken in a somewhat different direction and a portion of the tray has been cut away across a central well of the tray.

A preferred mixing tray for use with the dispenser 10 is illustrated in FIGS. 4-6 and is designated broadly by the numeral 60. The tray 60 includes a substrate 62 having an upper, generally horizontal wall section 61 and a pair of partial-spherical wall sections 63 that depend from the upper wall section 61 and define a pair of side wells 64. The tray 60 includes a central well 66 that is defined by a bottom wall section 65 and side wall sections 67 that also depend from the upper, horizontal wall section 61. The tray 60 also includes wall portions 69 that depend from the upper wall section 61 and define a pair of recesses 68.

The recesses 68 are located along opposite side wall sections 67 of the well 66. Each recess 68 is spaced above the bottom wall section 65 of the well 66 and has a volume that is less than the volume of the central well 66. The recesses 68 are spaced apart from each other a distance that matches the spacing between the outlets 18 of the dispenser 10.

In use, the mixing tray 60 is held or placed on a countertop or other surface in such a fashion that the upper wall section 61 of the mixing tray 60 extends in a horizontal plane. Next, the cap 38 is detached from the body 12 of the dispenser 10. The dispenser 10 is then held in a vertical orientation and moved to a position relative to the mixing tray 60 such that the two outlets 18 extend into the recesses 68 as depicted in FIG. 6.

Next, the lever 30 is depressed and moved toward its second position (as is shown in FIG. 6), causing the plunger 22 to advance and dispense material from each chamber 16 through the respective outlets 18. Once the lever 30 has reached its second position, the lever 30 is released and the spring 34 returns the lever 30 to its first position. The dispenser 10 is then lifted away from the mixing tray 60 if a sufficient amount of material has been dispensed, or alternatively the lever 30 is depressed again if an additional amount of material is desired.

The mixing tray 60 is especially useful for dispensing material such as dental adhesives when less than one drop of material from each chamber 16 is desired. As can be appreciated, such partial drops may not be sufficiently large to freely fall from the outlets 18. The recesses 68 enable the user to touch the front ends of the outlets 18 against the wall portions 69 defining the recesses 68, so that surface tension can thereafter pull the partial drops away from the ends of the outlets 18 and into the recesses 68 when the dispenser 10 is lifted away from the mixing tray 60.

The recesses 68, in combination with the well 66, are a particular advantage in that the likelihood of cross-contamination of material remaining in the containers 14 is substantially reduced. The recesses 68 help insure that the ends of each outlet 18 will not come into contact with other material in the well 66, such as material that has been dispensed from the opposite chamber 16. Once the material has been dispensed into the recesses 68, the material descends into the central well 66 to an area safely spaced away from the recesses 68. Moreover, because the side wall sections 67 are nearer to a vertical orientation than, for example, side walls of the wells 64 due to the larger diameter of the wells 64, it is less likely that material in the central well 66 will come into contact with the outlets 18 in instances when the mixing tray 60 is inadvertently tipped.

Preferably, the mixing tray 60 includes a sliding cover 70 (shown only in FIG. 4) that is received in channels located along opposite, upstanding walls of the substrate 62. The cover 70 is preferably made of a material that transmits at least part of the light in the visible wave length range so that dental material in the wells 64, 66 is visible when the cover 70 is closed, but also prevents transmission of a substantial portion of actinic radiation that might otherwise cause material in the wells 64, 66 to cure. The cover 70 can be shifted out of the way when access to the wells 64, 66 is desired. Further details of the cover 70 are set out in U.S. Pat. No. 5,377,823, which is expressly incorporated by reference herein.

Optionally, the mixing tray 60 also includes an opening 72 for bending a syringe tip or cannula. Further details of the opening 72 are set out in U.S. Pat. No. 5,295,827, which is expressly incorporated by reference herein. The substrate 62 is preferably made of a rigid plastic such as polypropylene.

Those skilled in the art may recognize that a number of other variations, modifications and additions are possible without departing from the spirit of the invention. For example, the dispenser of the invention is also useful when equipped with only a single chamber with a single plunger rod, or when equipped with more than two containers and a corresponding number of plunger rods. As another alternative, the containers may be in the form of a cartridge that is detachably coupled to the body 12. Consequently, the invention should not be deemed limited by the detailed description of the presently preferred embodiments set out above, but only by a fair scope of the claims that follow along with their equivalents.

We claim:

1. A dispenser comprising:

a body;

a first chamber connected to said body for containing a quantity of material to be dispensed, said first chamber including an outlet;

a liquid material in said chamber;

a plunger coupled to said body and movable relative to said body in an advancement direction toward said chamber; said plunger including a number of teeth arranged in a row;

a pawl for engagement with said teeth; and a lever pivotally coupled to said body and movable relative to said body between a released position and a fully depressed position, said lever being connected to said pawl for advancing said plunger as said lever is moved from said released position to said fully depressed position, said pawl moving over only a single tooth as said lever moves from said fully depressed position to said released position, and wherein movement of said lever from said released position to said fully depressed position enables no more than a single drop of said material to fall from said outlet.

2. The dispenser of claim 1, wherein movement of said lever from said released position to said fully depressed position enables less than a single, free drop of said material to be directed through said outlet opening.

3. The dispenser of claim 1, wherein said drop has a volume of less than 0.03 ml.

4. The dispenser of claim 1 and including a second chamber connected to said body for containing a second quantity of material to be dispensed, and including a mixing tray having an upper wall section, a well depending from said upper well section and a pair of recesses each depending from said upper well section, said recesses being located on opposite sides of said well, wherein said first chamber and said second chamber each include an outlet, wherein said outlet of said first chamber and said outlet of said second chamber are spaced apart a certain distance, and wherein said pair of recesses are spaced apart a distance that is approximately equal to said certain distance.

5. The dispenser of claim 1, wherein said chamber includes an outlet, and wherein said dispenser includes a cap detachably connected to said outlet, said cap including an arm in contact with said lever when said cap is connected to said outlet for retaining said lever in said first position.

6. The dispenser of claim 1, wherein said dispenser includes a stop connected to said lever and releasably engageable with said plunger in order to substantially preclude advancement of said plunger when said lever is in said first position.

7. A dispenser comprising:
   a body;
   a first chamber connected to said body for containing a quantity of material to be dispensed, said first chamber including an outlet;
   a plunger coupled to said body and movable relative to said body in an advancement direction toward said chamber;
   a lever pivotally connected to said body and movable relative to said body between a first position and a second position, said lever being connected to said plunger for advancing said plunger as said lever is moved from said first position to said second position; and
   a cap detachably connected to said outlet, said cap including an arm in contact with said lever when said cap is connected to said outlet for releasably retaining said lever in said first position.

8. The dispenser of claim 7, wherein said lever includes a forward end portion, and wherein said arm is in contact with said forward end portion of said lever when said cap is connected to said outlet.

9. The dispenser of claim 7 and including a second chamber connected to said body for containing a second quantity of material to be dispensed.

10. The dispenser of claim 9, wherein said cap includes keying structure for insuring said cap is in a certain, single orientation relative to said first chamber and said second chamber when said cap is connected to said outlet.

11. The dispenser of claim 9, and including a mixing tray having an upper wall section, a well depending from said upper well section and a pair of recesses each depending from said upper well section, said recesses being located on opposite sides of said well, wherein said second chamber includes an outlet, wherein said outlet of said first chamber and said outlet of said second chamber are spaced apart a certain distance, and wherein said pair of recesses are spaced apart a distance that is approximately equal to said certain distance.

12. The dispenser of claim 7 and including a container defining said chamber, wherein said container is integral with said body.

13. The dispenser of claim 7, wherein said plunger includes at least one row of teeth, and wherein said dispenser includes a stop connected to said lever for engagement with said row of teeth in order to substantially preclude advancement of said plunger when said lever is in said first position.

14. A dispenser comprising:
    a body;
    a first chamber connected to said body for containing a quantity of material to be dispensed, said first chamber including an outlet;
    a plunger coupled to said body and movable relative to said body in an advancement direction toward said chamber;
    a lever pivotally connected to said body and movable relative to said body between a first position and a second position, said lever being coupled to said plunger for advancing said plunger as said lever is moved from said first position to said second position; and
    a stop connected to said lever and in contact with said plunger when said lever is in said first position in order to substantially preclude advancement of said plunger when said lever is in said first position, said stop being out of contact with said plunger when said lever is in said second position.

15. The dispenser of claim 14, wherein said lever includes an end portion and wherein said stop is directly connected to said end portion of said lever.

16. The dispenser of claim 14, wherein said stop comprises a set of teeth.

17. The dispenser of claim 14 and including a container defining said chamber, and wherein said container is integrally connected to said body.

18. The dispenser of claim 17, wherein said dispenser includes a cap detachably connected to said outlet, said cap including an arm in contact with said lever when said cap is connected to said outlet for retaining said lever in said first position.

19. The dispenser of claim 14 and including a second chamber connected to said body for containing a second quantity of material to be dispensed.

20. The dispenser of claim 19, and including a mixing tray having an upper wall section, a well depending from said upper wall section and a pair of recesses each depending from said upper wall section, said recesses being located on opposite sides of said well, wherein said second chamber includes an outlet, wherein said outlet of said first chamber and said outlet of said second chamber are spaced apart a certain distance, and wherein said pair of recesses are spaced apart a distance that is approximately equal to said certain distance.

21. An assembly comprising:
    a mixing tray comprising a substrate having an upper, generally horizontal wall section, side wall sections depending from said upper wall section and a bottom wall section connected to said side wall sections, said side wall sections and said bottom wall section defining a mixing well having a certain volume, said substrate also including wall portions depending from said upper wall section and presenting a pair of recesses located along said side wall sections, each of said recesses having a volume that is less than said certain volume of said mixing well and being in communication with said mixing well, each of said recesses being located above said bottom wall section to enable material dispensed into said recesses to flow by gravity into said mixing well; and
    a dispenser having a first chamber with an outlet and a second chamber with an outlet, wherein said outlet of said first chamber and said outlet of said second chamber are spaced apart a certain distance, and wherein said pair of recesses are spaced apart a distance that is approximately equal to said certain distance.

22. The mixing tray of claim 21, wherein said side wall sections include a pair of wall sections located along opposite sides of said mixing well, and wherein each of said recesses is located along a respective one of said pair of side wall sections.

23. The mixing tray of claim 21, and including a cover slidably connected to said substrate.

24. The mixing tray of claim 23, wherein said cover is made of a material that transmits light in the visible range and is substantially opaque to the transmission of actinic radiation.

\* \* \* \* \*